(12) United States Patent
Tzortzis

(10) Patent No.: US 11,241,449 B2
(45) Date of Patent: Feb. 8, 2022

(54) GALACTOOLIGOSACCHARIDE COMPOSITION FOR USE IN PREVENTING OR TREATING COGNITIVE DYSFUNCTION AND EMOTIONAL DISTURBANCES IN NEUROPSYCHIATRY ILLNESSES OR AGEING

(71) Applicant: Clasado Inc., Panama (PA)

(72) Inventor: Georgios Tzortzis, Reading (GB)

(73) Assignee: CLASADO RESEARCH SERVICES LIMITED, Reading (GB)

( * ) Notice: Subject to any disclaimer, the term of this patent is extended or adjusted under 35 U.S.C. 154(b) by 0 days.

(21) Appl. No.: 14/780,461

(22) PCT Filed: Mar. 17, 2014

(86) PCT No.: PCT/GB2014/050829
§ 371 (c)(1),
(2) Date: Sep. 25, 2015

(87) PCT Pub. No.: WO2014/155056
PCT Pub. Date: Oct. 2, 2014

(65) Prior Publication Data
US 2016/0045524 A1 Feb. 18, 2016

(30) Foreign Application Priority Data
Mar. 28, 2013 (GB) .................. 1305708

(51) Int. Cl.
*A61K 31/702* (2006.01)
*A61K 31/70* (2006.01)
*A61P 25/24* (2006.01)
*A61K 31/7016* (2006.01)

(52) U.S. Cl.
CPC ............ *A61K 31/70* (2013.01); *A61K 31/702* (2013.01); *A61K 31/7016* (2013.01); *A61P 25/24* (2018.01)

(58) Field of Classification Search
CPC .............. A61K 31/702; A61K 31/7016; A61K 2300/00
USPC ......... 514/54, 61, 53, 23; 536/123.1, 123.13
See application file for complete search history.

(56) References Cited

U.S. PATENT DOCUMENTS

| 2010/0016214 A1 | 1/2010 | Sawatzki et al. |
| 2012/0276208 A1 | 11/2012 | Best |
| 2012/0315630 A1* | 12/2012 | Gong ................... C12Q 1/6827 435/6.11 |

FOREIGN PATENT DOCUMENTS

| EP | 1 644 482 | 4/2006 |
| EP | 2 014 181 A2 | 1/2009 |
| TW | 201000108 A1 | 1/2010 |
| WO | WO 2005/003329 | 1/2005 |
| WO | WO 2010/023422 A1 | 3/2010 |
| WO | WO 2010/105207 A1 | 9/2010 |

OTHER PUBLICATIONS

Minden (Journal of NeuroVirology (2000) 6, Supp 2, SI60-SI67).*
Paparrigopoulos et al. (International Review of Psychiatry, Feb. 2010; 22(1): 14-21).*
Silk et al. (Alimentary Pharmacology Therapeutics, 2009; 29, 508-518).*
Cardenas-Aguayo et al. (PloS one, (2013) vol. 8, No. 1, pp. e53596, 1-18). Electronic Publication Date: Jan. 8, 2013).*
Modabbernia et al. (BMC Research Notes 2012, 5:112).*
Sachar et al. (Arch Gen Psychiatry. 1973;28(1):19-24) (abstract sent).*
Fischer et al. (Psychoneuroendocrinology (2012) 37, 1712-1718).*
Anthony, Joshua C. et al.; 90-Day oral (gavage) study in rats with galactooligosaccharides syrup; Food and Chemical Toxicology; vol. 44; Iss. 6; Jun. 2006; pp. 819-826.
Autry, Anita E. et al.; "NMDA Receptor Blockade at Rest Triggers Rapid Behavioural Antidepressant Responses"; Nature; 475(7354); Jun. 15, 2011; pp. 91-95.
Bassi, Gabriel S. et al.; "Lipopolysaccharide-Induced Sickness Behaviour Evaluated in Different Models of Anxiety and Innate Fear in Rats"; BCPT; vol. 110; Iss. 4; Apr. 2012; pp. 359-369.
Bercik, Premysl et al.; "The anxiolytic effect of Bifidobacterium longum NCC3001 involves vagal pathways for gut-brain communication"; Neurogastroenterol Motil.; Dec. 2011; 23(12); pp. 1132-1139.
Bercik, Premysl et al.; "The Intestinal Microbiota Affect Central Levels of Brain-Derived Neurotropic Factor and Behavior in Mice"; Gastroenterology; 2011; 141; pp. 599-609.
Bissonette, Gregory B. et al.; "Neural structures underlying set-shifting: roles of medial prefrontal cortex and anterior cingulate cortex"; Behav Brain Res.; Aug. 1, 2013; 250; pp. 91-101.
Bourin, Michel et al.; "The mouse light/dark box test"; European Journal of Pharmacology; vol. 463; Iss. 1-3; Feb. 28, 2003; pp. 55-65.
Browning, M. et al.; "A single dose of citalopram increases fear recognition in healthy subjects"; J Psychopharmacol.; Sep. 2007; 21(7); pp. 684-690.
Burnet, Philip W. J.; "Gut bacteria and brain function: The challenges of a growing field"; PNAS; Jan. 24, 2012; vol. 109; No. 4; E175; 1pg.
Coyle, Joseph T.; "NMDA Receptor and Schizophrenia: A Brief History"; Schizophr Bull.: Sep. 2012; vol. 38; No. 5; pp. 920-926.
Cryan, John F. et al.; Mind-altering microorganisms: the impact of the gut microbiota on brain and behaviour; Nature Reviews Neuroscience 13; Oct. 2012; pp. 701-712.
Deacon, Robert M. J.; "Digging and marble burying in mice: simple methods for in vivo identification of biological impacts"; Nat Protoc.; 2006;1(1); pp. 122-124.

(Continued)

*Primary Examiner* — Shaojia A Jiang
*Assistant Examiner* — Michael C Henry
(74) *Attorney, Agent, or Firm* — Lewis Roca Rothgerber Christie LLP

(57) ABSTRACT

A galactooligosaccharide composition comprising a mixture of disaccharides, trisaccharides, a tetrasaccharide and a pentasaccharide for use in preventing or treating cognitive dysfunction and/or emotional disturbances in neuropsychiatric illnesses or ageing.

15 Claims, 8 Drawing Sheets

(56) References Cited

OTHER PUBLICATIONS

Eastwood, Sharon L. et al.; "Altered expression of synaptic protein mRNAs in STOP (MAP6) mutant mice"; Journal of Psychopharmacology; vol. 21; Iss. 6; 2007; pp. 635-644.
Grant, Suzanne L. et al.; "Determination of D-serine and related neuroactive amino acids in human plasma by high-performance liquid chromatography with fluorimetric detection"; Journal of Chromatography B; vol. 844; Iss. 2; Dec. 5, 2006; pp. 278-282.
Harmer, Catherine J. et al.; "Increased positive versus negative affective perception and memory in healthy volunteers following selective serotonin and norepinephrine reuptake inhibition"; Am J Psychiatry.; Jul. 2004; 161(7); pp. 1256-1263.
Kerman, Ilan A.: "New Insights Into BDNF Signaling: Relevance to Major Depression and Antidepressant Action"; Am J Psychiatry.; Nov. 2012; 169(11); pp. 1137-1140.
Morikawa, Akiko et al.; "Determination of free D-aspartic acid, D-serine and D-alanine in the brain of mutant mice lacking D-amino-acid oxidase activity"; J Chromatogr B Biomed Sci Appl.; Jun. 5, 2001; 757(1); pp. 119-125.
Murphy, Susannah E. et al.; "Short-term serotonergic but not noradrenergic antidepressant administration reduces attentional vigilance to threat in healthy volunteers"; Int J Neuropsychopharmacol.; Mar. 2009: 12(2); pp. 169-179.
Nicolas, Laurent B. et al.; "A combined marble burying-locomotor activity test in mice: A practical screening test with sensitivity to different classes of anxiolytics and antidepressants": European Journal of Pharmacology: vol. 547; Iss. 1-3; Oct. 10, 2006; pp. 106-115.
Njung'e, Kung'u et al.; "Evaluation of marble-burying behavior as a model of anxiety"; Pharmacology Biochemistry and Behavior; vol. 38; Iss. 1, Jan. 1991; pp. 63-67.
O'Leary, Timothy P. et al.; "The effects of apparatus design and test procedure on learning and memory performance of C57BL/6J mice on the Barnes maze"; Journal of Neuroscience Methods; vol. 203; Iss. 2; Jan. 30, 2012; pp. 315-324.

O'Sullivan, E. et al.; "BDNF expression in the hippocampus of maternally separated rats: does Bifidobacterium breve 6330 alter BDNF levels?"; Beneficial Microbes; 2(3); Sep. 2011; pp. 199-207.
Skelly, Donal T. et al.; "A Systematic Analysis of the Peripheral and CNS Effects of Systemic LPS, IL-1B, TNF-a and IL-6 Challenges in C57BL/6 Mice"; PLoS One; Jul. 2013; vol. 8; Iss. 7; e69123; 20pp.
Soriano, Francesc X. et al.; "Preconditioning Doses of NMDA Promote Neuroprotection by Enhancing Neuronal Excitability"; J Neurosci.; Apr. 26, 2006; vol. 26; No. 17; pp. 4509-4518.
Strekalova, Tatyana et al.; "Stress-Induced Anhedonia in Mice is Associated with Deficits in Forced Swimming and Exploration"; Neuropsychopharmacology: 2004; 29; pp. 2007-2017.
Treit, Dallas et al.; "Conditioned defensive burying: a new paradigm for the study of anxiolytic agents"; Pharmacol Biochem Behav.; Oct. 1981; 15(4); pp. 619-626.
Bravo, Javier A. et al.; "Ingestion of *Lactobacillus* strain regulates emotional behavior and central GABA receptor expression in a mouse via the vagus nerve"; PNAS; Sep. 2011; vol. 108; No. 38; pp. 16050-16055.
Depeint, Flore et al.; "Prebiotic evaluation of a novel galactooligosaccharide mixture produced by the enzymatic activity of Bifidobacterium bifidum NCIMB 41171, in healthy humans: a 13 randomized, double-blind, crossover, placebo-controlled intervention study[1-3]"; Am J Clin Nutr; 2008; 87; pp. 785-791.
GB Search Report for corresponding Application No. GB1405503. 2, dated Nov. 3, 2014, 2pp.
Logan, Alan C. et al.; "Major depressive disorder: probiotics may be an adjuvant therapy"; Medical Hypotheses; 64; 2005; pp. 533-538.
TW Search Report for corresponding Application No. TW 103111198, dated Mar. 19, 2015, 1pg.
Cosco, T.D. et al., Latent Structure of the Hospital Anxiety and Depression Scale: A 10-year systematic review, Journal of Psychosomatic Research, vol. 72, 2012, pp. 180-184.
Coyne, J.C. et al., No further research needed: Abandoning the Hospital and Anxiety Depression Scale (HADS), Journal of Psychosomatic Research, vol. 72, 2012, pp. 173-174.

* cited by examiner

*differences between Day 0 and Day 21 are significant at p=.05 (for Time 30, Groups B and C), at trend at p=.1 (Time 45, Group C)

Frontal Cortex:

Plasma:

GALACTOOLIGOSACCHARIDE COMPOSITION FOR USE IN PREVENTING OR TREATING COGNITIVE DYSFUNCTION AND EMOTIONAL DISTURBANCES IN NEUROPSYCHIATRY ILLNESSES OR AGEING

CROSS-REFERENCE TO RELATED APPLICATION(S)

This application is a National Phase Patent Application and claims priority to and the benefit of International Application Number PCT/GB2014/050829, filed on Mar. 17, 2014, which claims priority to Great Britain Patent Application Number 1305708.8, filed on Mar. 28, 2013, the entire contents of all of which are incorporated herein by reference.

The present invention relates to a composition comprising a mixture of galactooligosaccharides (GOS) for use in preventing or treating cognitive dysfunction and/or emotional disturbances occurring in neuropsychiatric illnesses or disorders, or in aging in a human. It also relates to a method of preventing or treating cognitive dysfunction and/or emotional disturbances occurring in neuropsychiatric illnesses or disorders, or in aging by orally administering to an individual an effective amount of a composition comprising a mixture of galactooligosaccharides.

Preventing of a disease refers to the ability of a pharmaceutical composition or treatment to not only prevent the occurrence of disease, such as risk factor reduction, but also to arrest its progress and reduce its consequences once established (Ref: adapted from Glossary of Terms used in Health for All Series. WHO, Geneva, 1984).

Primary prevention is directed towards preventing the initial occurrence of a disorder whereas secondary and tertiary prevention seeks to arrest or retard existing disease and reduce occurrence of relapses and establishment of chronic conditions.

Cognitive dysfunction refers to the loss of intellectual functions, such as thinking, remembering and reasoning, of sufficient severity to interfere with daily functioning of the individual. This can be seen in aging and dementia sufferers, especially in people suffering from Alzheimer's disease. Impairment of cognitive function can affect the ability to think, to concentrate, to formulate ideas, to reason and to remember.

Neuropsychiatric illnesses or disorders refers to organic cerebral disorders or neurological disorders that cause psychiatric symptoms. They include anxiety disorders and depressive disorders that commonly occur in elderly patients.

A review by Cryan, J F and Dinan, T G in Nature Review/Neuroscience; 13; 701-712: (2012) describes how studies in germ-free animals and in animals exposed to pathogenic bacterial infections, probiotic bacteria or antibiotic drugs suggest a role for the gut microflora in the regulation of anxiety, mood, cognition and pain.

Probiotic bacteria are defined as live bacteria that may confer a health benefit on the host if ingested.

Bravo, J A et al demonstrated antidepressant and anxiolytic-like properties of the probiotic *Lactobacillus rhamnosus* when ingested by mice (see Proc Nath Acad Sci USA; 108; 16050-16055; (2011)).

Burnet, P W J suggested that future studies using selective antimicrobials and prebiotics to increase strains of lactobacilli and bifidobacteria indigenous to the gut may have an effect on behaviours and neurophysiological outputs in animals and humans (see Proc. Natl. Acad. Sci. USA; E175; (2012)).

Prebiotics are defined as non-digestible food ingredients that beneficially affect the host by selectively stimulating the growth and/or activity of one or a limited number of bacteria in the colon, thereby resulting in an improvement in the health of the host. Galactooligosaccharides (GOS) and fructooligosaccharides (FOS) are examples of prebiotics that are resistant to mammalian gastrointestinal digestive enzymes but are fermented by specific colonic bacteria.

It has now been found that oral administration to a mammal, such as a human, of a composition comprising a mixture of galactooligosaccharides can result in a direct interaction with the neurons located in the gastrointestinal tract, that in turn may result in an unexpected increase in the levels of N-methyl-D-aspartate receptors (NMDARs). Specifically, elevated levels of the NMDAR NRI protein and/or mRNA in both the cortex and the hippocampus part of the brain were found, and also of the NMDAR NR2A protein in the hippocampus. This suggested that the compositions comprising such a mixture may be beneficial in preventing or treating cognitive dysfunction and/or emotional disturbances occurring in neuropsychiatric illnesses or disorders, or in aging.

It has also been found that oral administration of a GOS composition lowers the secretion of cortisol. Since cortisol is released in response to stress this suggests that the composition may reduce the exaggerated cortisol secretion that is symptomatic of anxiety disorders and depressive disorders.

The mixture of galactooligosaccharides comprised disaccharides Gal (ß1-3)-Glc; Gal (ß 1-3)-Gal; Gal (ß 1-6)-Gal; Gal (α 1-6)-Gal; trisaccharides Gal (ß1-6)-Gal (ß1-4)-Glc; Gal (ß1-3)-Gal (ß1-4)-Glc; tetrasaccharide Gal (ß1-6)-Gal (ß1-6)-Gal (ß1-4)-Glc and pentasaccharide Gal (ß1-6)-Gal (ß1-6)-Gal (ß1-6)-Gal (ß1-4)-Glc.

This mixture of galactooligosaccharides is disclosed in EP 1 644 482, which describes a novel strain of *Bifidobacterium bifidum* that produces a galactosidase enzyme activity that converts lactose to this novel mixture of galactooligosaccharides. This novel mixture has been shown to have prebiotic and anti-inflammatory properties in the gut.

This mixture of galactooligosaccharides is marketed commercially under the name of Bimuno (registered trade mark) and is available from Clasado Ltd (Milton Keynes, UK).

According to one aspect of the invention there is provided a composition comprising a mixture of galactooligosaccharides as defined above for use in preventing or treating cognitive dysfunction and/or emotional disturbances occurring in neuropsychiatric illness or disorders, or in aging.

According to a second aspect of the invention there is provided the use of a mixture of galactooligosaccharides as defined above in the preparation of a medicament for preventing or treating cognitive dysfunction and/or emotional disturbances occurring in neuropsychiatric illness or disorders, or in aging.

The cognitive dysfunction may be cognitive decline or impairment as a result of aging, dementia or schizophrenia. The neuropsychiatric illness may be depressive disorders or anxiety disorders. Anxiety disorders covers several different forms of a type of common psychiatric disorder characterised by excessive rumination, worrying, uneasiness, apprehension and fear about future uncertainties either based on real or imaged events which may effect both physical and psychological health.

According to yet another aspect of the invention there is provided a method of preventing or treating cognitive dysfunction and/or emotional disturbances occurring in neuropsychiatric illness or in aging comprising administering to an individual, such as a human, an effective amount of a composition comprising a mixture of galactooligosaccharides as defined above. An effective amount of the galactooligosaccharide composition is preferably administered daily as a single dose or alternatively as two separate doses several hours apart, for example from 4 to 12 hours apart, preferably from 6 to 10 hours apart, most preferably 8 hours apart.

Preferably, the composition or mixture of galactooligosaccharides is administered orally on a daily basis in the form of a freeze-dried powder, a tablet, a capsule, a liquid formulation such as a syrup, or a soft pastille.

The product known as Bimuno comprises at least 49% of the dry matter as the mixture of galactooligosaccharides. The remainder of the composition may comprise non-active components such as glucose, galactose, lactose, acacia gum, maltodextrin and citric acid.

The powder composition preferably comprises from 1.35 g to 9.6 g of galactooligosaccharide in 1.65 g to 20 g of the powdered composition, preferably from 1.96 g to 4.9 g of galactooligosaccharide in 2.5 g to 10 g of the powder, most preferably 2.7 g to 2.75 g of galactooligosaccharide in 3.0 g to 5.5 g of composition. The composition may be added to a drink, preferably a hot drink, or sprinkled on food, for example, on breakfast cereal. The composition may also be added as an ingredient to various foodstuffs and drinks such as fruit juice, fruit drinks, water, coffee, yoghurt, cereals, bread, cakes, biscuits and the like.

Alternatively, the galactooligosaccharide may be presented as a syrup or pastille (dehydrated syrup) in which the non-active components may comprise glucose, galactose, lactose and citric acid. A daily dose of the syrup may comprise from 1.35 g to 9.6 g of the galactooligosaccharide mixture in 2.1 g to 25.29 g of the syrup composition, preferably from 1.96 g to 4.9 g of galactooligosaccharide in 3.0 g to 12.9 g of the syrup, most preferably 2.7 g to 2.75 g of galactooligosaccharide in 4.1 g to 7.25 g of the syrup.

The galactooligosaccharide composition of the invention has anxiolytic properties, reduces the activity of the hypothalamic-pituitary axis (stress hormone secretion) and reduces inflammatory responses in the brain. Thus Bimuno GOS may be beneficial in the treatment or prevention of anxiety disorders (e.g. worry, insomnia), depressive disorders, brain inflammation caused by bacterial meningitis, Herpes Simplex encephalitis or that occurs in Alzheimer's disease. Bimuno GOS may also improve cognitive impairment in ageing, dementia and schizophrenia. Furthermore, the GOS composition may benefit the detrimental influence of maternal infection on the developing foetal brain.

The invention will be further described by way of reference to the following examples and figures.

FIGS. 3A to 3F are representative auto-radiographs of BDNF (A, C, E) and NRI subunit (B, D, F) mRNA expression in rat hippocampus following oral administration of water (A, B), FOS (C, D) or GOS (E, F). Arrows delineate increased expression and arrow head indicates reduced expression. DG=dentate gyrus, CA1 and CA3=Cornu Ammons subfields of the hippocampus. Scale bar=200 μM.

FIGS. 4A to 4D show the effect of FOS and GOS on levels of BDNF, NR1, NR2A and NR2B mRNAs in the dentate gyrus (DG) and CA1 and CA3 (Cornu Ammons) subfields of the hippocampus.

Figure 5:
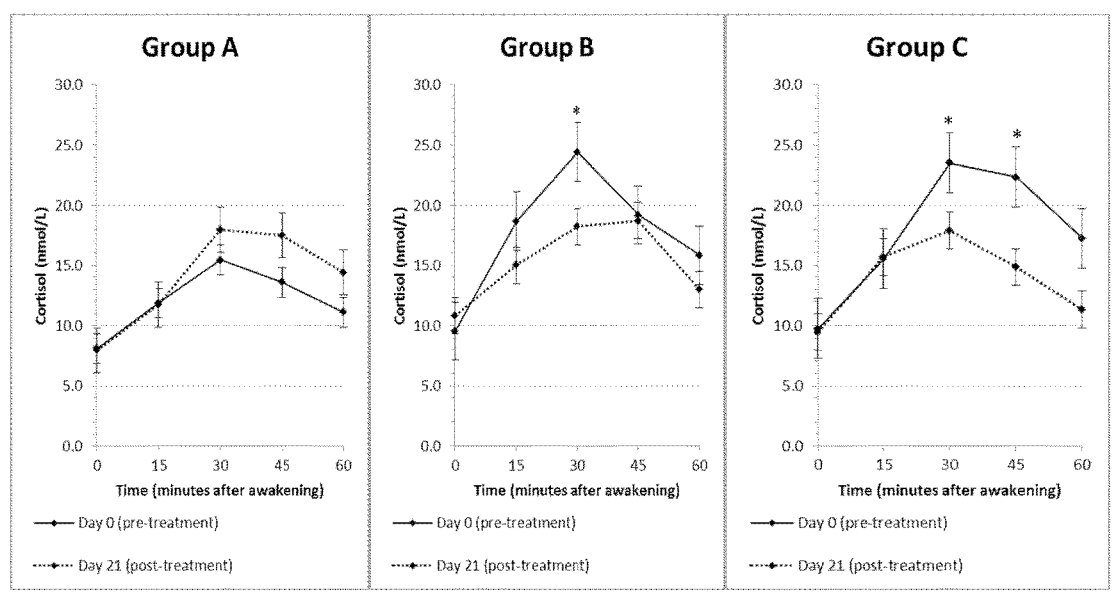

FIG. 5 shows the effect on cortisol secretion in healthy adults following ingestion of FOS (Group A), GOS (Group C) and a placebo (Group B).

Figure 6:
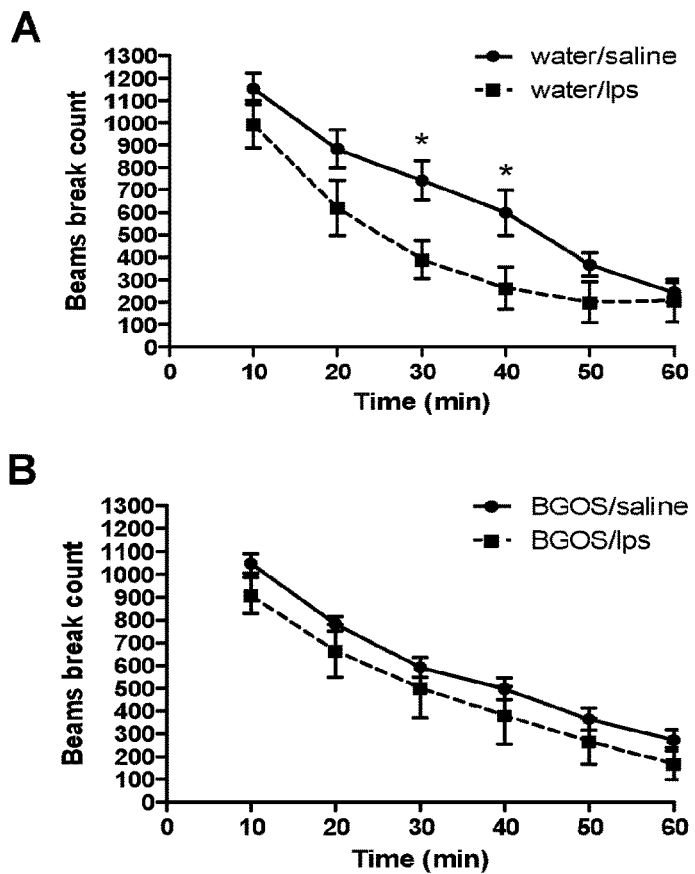

FIG. 6A shows the effect on locomotor activity in water-fed mice following lipopolysaccharide (LPS) injection.

FIG. 6B shows how GOS abolished the LPS effect on locomotor activity.

Figure 7:
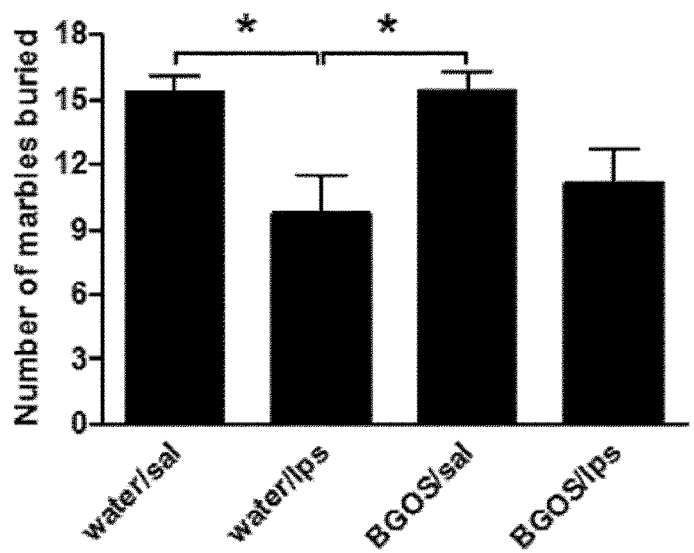

FIG. 7 shows the effect on natural digging and burying behaviour, as shown in the marble burying test, in mice following LPS treatment.

Figure 8:
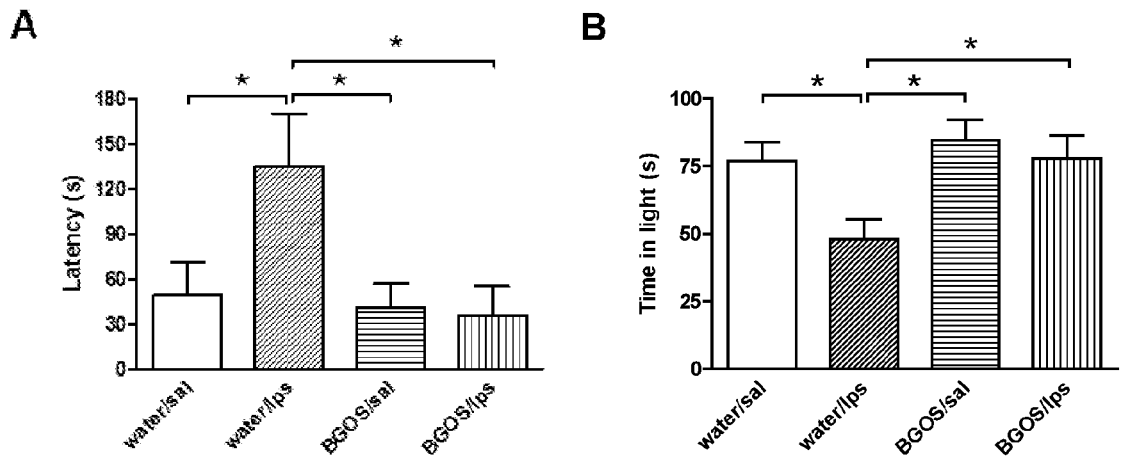

FIG. 8 shows the effect on anxiety behaviour in mice following LPS treatment. Latency (A)=time taken to move from dark (less stressful) to light (more stressful) areas. Greater latency=more stressed/reduced exploratory behaviour. Time in light (B)=time spent in light area. Greater time=less anxious.

Figure 9:
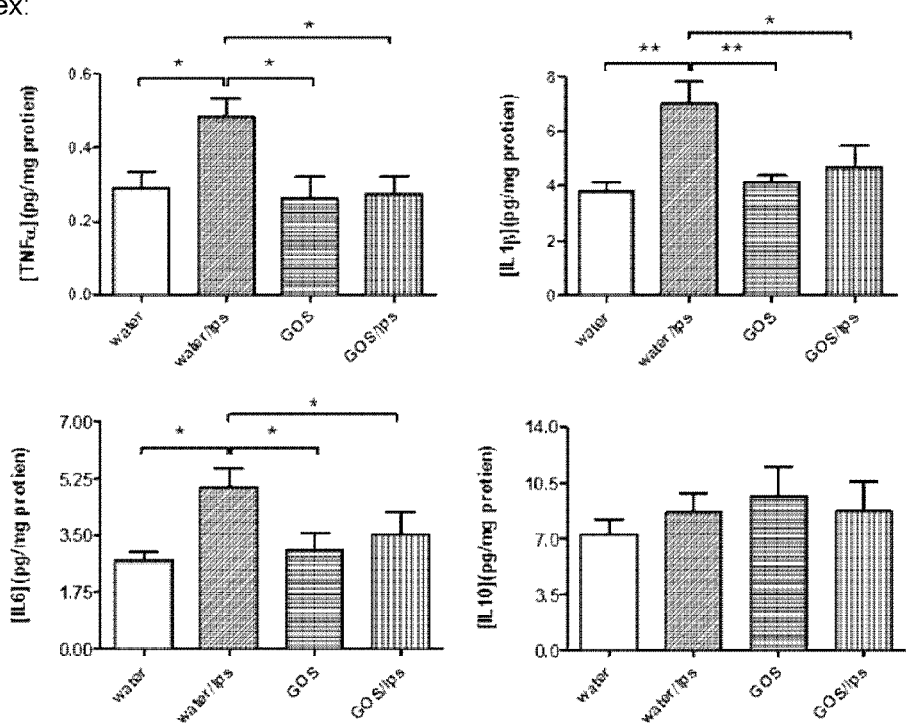

FIG. 9 shows the effect on cytokine levels in the frontal cortex of mice 24 hours after LPS injection.

Figure 10:
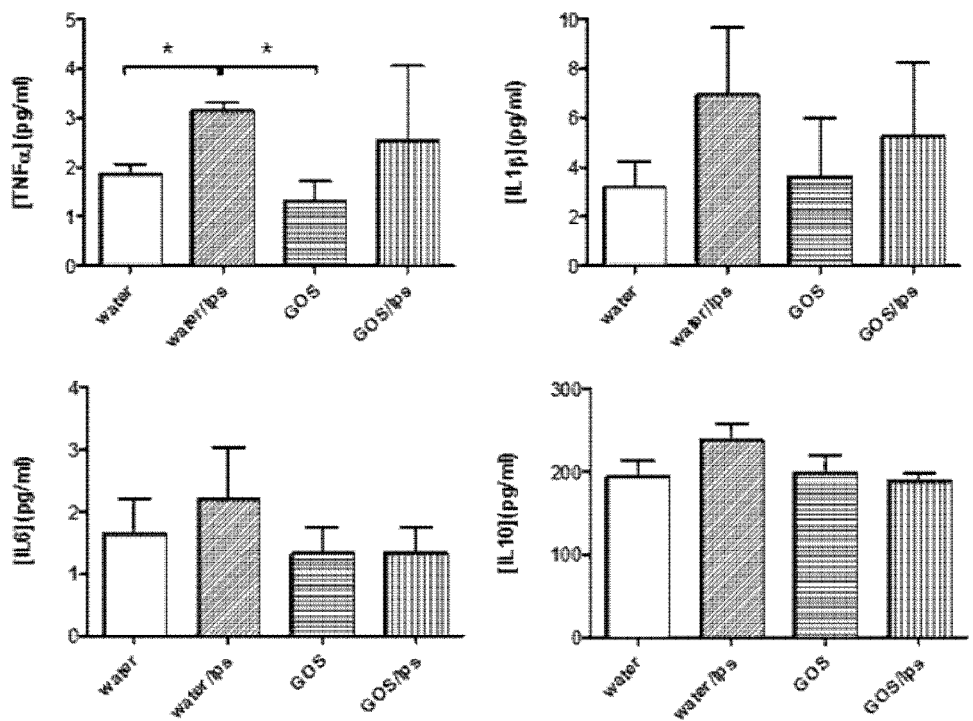

FIG. 10 shows the effect on cytokine levels in the plasma of mice 24 hours after LPS injection.

Figure 11:
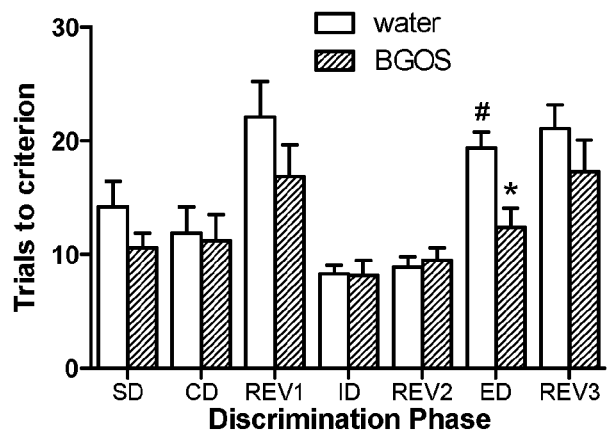

FIG. 11 shows the effect of BGOS on cognitive performance in healthy rats.

EXAMPLE 1

Freeze-Dried Powdered Composition Packaged in a 'Stick-Pack' and Containing Per 5.5 g Final Product

| | |
|---|---|
| Galactooligosaccharide (GOS) mixture | 2.75 g |
| Lactose | 1.40 g |
| Monosaccharides (glucose, galactose) | 0.64 g |
| Drying aid | 0.24 g |
| Ash | 0.23 g |
| Moisture | 0.19 g |
| Protein | 0.05 g |

EXAMPLE 2

Syrup Composition Per 7.25 g Finished Product

| | |
|---|---|
| Galactooligosaccharide (GOS) mixture | 2.75 g |
| Lactose | 0.58 g |
| Monosaccharides (glucose, galactose) | 1.69 g |
| Ash | 0.23 g |
| Moisture | 1.95 g |
| Protein | 0.05 g |

EXAMPLE 3

In Vivo Study of the Effect of Feeding Prebiotics on Central Brain Derived Neurotrophic Factor (BDNF) and N-Methyl-D-Aspartate (NMDA) Receptor Subunits Materials and Methods
Prebiotic Administration All rat experiments were carried out in accordance with UK Home Office guide lines and under approved licenses. Male Sprague Dawley rats (225-250 g) were administered a daily oral administration (gavage) of either water, FOS (fructooligosaccharide) (4 g/kg) or GOS (galactooligosaccharide [Bimuno]) (4 g/kg), for 5 weeks (n=8/group). This dosing regimen was based on previous studies (Anthony et al; Food Chem Toxicol.; 44 (6); 819-26 (2006)) and pilot data showing that these optimal prebiotic doses provides maximum microbiota growth (not shown). All animals were sacrificed, trunk blood collected and their brains removed, twenty-four hours after the last gavage. Blood was centrifuged to obtain plasma, and the frontal cortex and hippocampus were dissected out from half of the harvested brains. Whole brains and isolated regions were snap-frozen in isopentane on dry-ice and stored with plasmas at −80° C. prior to use.

BDNF Analysis

Cortex and hippocampus tissue from all groups were homogenized in RIPA (radio immunoprecipitation assay) buffer (1:10 w/v, Sigma Aldrich, UK) containing protease inhibitors ('Complete-Mini', Roche). Protein concentrations were determined using the Bradford reagent (Sigma, UK). Samples of protein extracts were diluted 1:5 v/v in deionised water, prior to their analysis with a commercial BDNF ELISA kit (BDNF Emax immunoassay system, Promega UK).

Western Blotting

Equal concentrations of protein extracts of cortex, hippocampus or cerebellum (20 µg) from prebiotic and control groups were mixed with loading buffer (50 mM 1,4-dithiothreitol and 0.025% bromophenol blue), and fractionated with a molecular weight marker (GE Healthcare, Buckinghamshire, UK) by electrophoresis on pre-cast 7.5% SDS/polyacrylamide gels (Biorad, UK), and trans-blotted onto polyvinyl difluoride (PVDF) membranes (Immobilon-P, Millipore, Watford, UK).

The membranes were blocked with 5% (w/v) non-fat milk in PBS (phosphate buffered saline) containing 0.1% Tween (PBST) for 45 min, and then incubated for 1 h at room temperature in incubation buffer (PBST with 2% [w/v] milk) containing a primary antibody (diluted 1:1000) against one of three NMDAR subunits: NR1 (AB9864, Millipore, UK), NR2A (AB1555, Millipore, UK) and NR2B (AB15362, Millipore, UK), and b-actin (Sigma-Aldrich, UK, diluted 1:50,000). Membranes were then washed three times for ten minutes in PBST and incubated for 30 min in HRP (horseradish peroxidise)-linked secondary antibody in blocking buffer. Immunoreactive bands were visualized by chemiluminescence using the ECL-Plus kit (GE Healthcare, Buckinghamshire, UK), and apposing membranes to X-ray film (Kodak BioMax AR film). All antibodies produced a single band of expected molecular weight. The optical densities (OD) of bands were measured using the Alphalmager 3400, and the data expressed as OD ratios of phosphorylated:total NMDAR subunit, or total NMDAR subunit:b-actin.

In Situ Hybridization Histochemistry (ISHH)

The frozen rat brain hemispheres were coronally sectioned (14 µm) on a cryostat, thaw mounted on to Superfrost-plus slides (Fisher Scientific) and stored at −80° C. Sections containing frontal cortex were pre-treated as described (Burnet et al; Mol. Cell. Neurosci.; 46; 167-75; (2011)).

Commercially synthesized (MWG, UK) oligodeoxyribonucleotides complementary to: BDNF (bases 883-927, NM001270630.1), NR1 (bases 746-780, NM008169.1), NR2A (bases 1642-1676, NM008170.2) or NR2B (bases 1758-1792, NM010350.2) were used in an establish ISHH method (Eastwood et al.; J. Psychopharmacol.; 21; 635-644; (2007)). Oligodeoxyribonucleotide probes were 3'-end labelled with [$^{35}$S]-dATP using terminal deoxynucleotidyl transferase (Promega, UK). Probes were diluted in hybridization buffer, pipetted onto the tissue sections ($1 \times 10^6$ cpm/section), cover-slipped and then incubated for >16 hrs at 34° C. lidded Perspex trays lined with filter paper soaked with 4×SSC (saline sodium citrate)/50% formamide.

Post-hybridization washes included: 2×SSC rinse at room temperature to remove cover-slips; 0.5×SSC, 20 min (×3) at 55° C.; 0.5×SSC 30 min (×2) at room temperature. Slides were rinsed in ddH$_2$O, dried and apposed to X-ray film (Kodak, Biomax MS) for 7-28 days with $^{14}$C-microscales. Average grey densities across the depth of the frontal cortex grey matter were measured for each of the mRNAs using computer-assisted image analysis, and converted to nCi/mg tissue using $^{14}$C-microscale standards.

HPLC Analysis

Small fragments of the cortical tissue (50 mg) were individually homogenized in ice-cold methanol (1:10 w/v) and microfuged at 13200 rpm for 10 minutes at 4° C. Supernatants (10 µl) were injected onto a Hewlett-Packard 1100 liquid chromatograph (Agilent Technologies, Palo Alto, Calif.) and subjected to online, pre-column, derivatization as previously described (Grant et al; J. Chromatogr. B Analyt. Technol. Biomed. Life Sci.; 844; 278-282 (2006)). Briefly, samples (10 µl) were reacted with an equal volume of derivatizing reagent [o-phthaldialdehyde (2 mg) and Boc-L-cysteine (2 mg) in 0.2 ml of methanol and 0.8 ml of 0.4M of sodium borate buffer (pH=9)], for 5 min prior to column separation. Separation was achieved using an Agilent Zorbax Eclipse XDB-C18 column (4.6×150 mm, 5 µm) maintained at 30° C. and a separation protocol similar to that of (Morikawa et al; J. Chromatogr. B. Biomed. Sci. Appl.; 757; 119-25 (2001)). The mobile phases consisted of acetonitrile (phase A) and 100 mM Sodium acetate buffer pH=6 (phase B) and were pumped through the column at 1.4 ml/min. The following gradient system was used (min/% B): 0/91, 35/84, 65/84. Detection of derivatized amino acids was by fluorescence detection (emission: 443 nm; excitation 344 nm). Eight point calibration curves of the D- and L-amino acids (Sigma Aldrich, UK) were constructed using authentic standards (0.5 to 1000 pmol) and in each case were found to be linear with correlation coefficients of >0.995.

Data Analysis

All data were expressed as mean±standard error of the mean (SEM). Statistical comparisons between groups were performed with one-way ANOVA followed by post hoc analysis (Tukey HSD).

Results
Bifidobacteria in Faecal Pellets from Control and Prebiotic Rats

The numbers of bifidobacteria in faecal pellets (expressed as log 10/g) from FOS-fed rats were significantly greater than controls (9.498±0.025 vs 9.354±0.055, p<0.05), whereas the density of bifidobacteria from GOS-fed animals were significantly greater than both controls (9.624±0.05 vs 9.354±0.055, p<0.01) and FOS-fed rats (9.624±0.05 vs 9.498±0.025, p<0.05).

Figure 1:
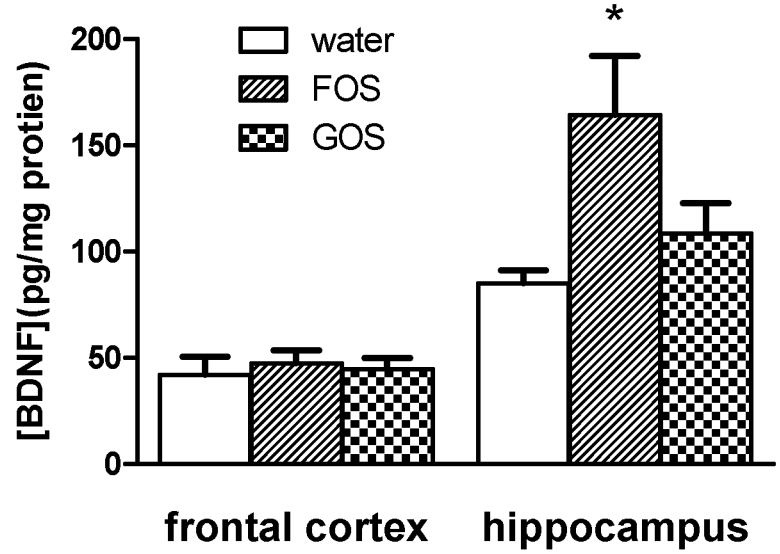
FIG. 1A shows the effect of FOS and GOS on levels of BDNF protein in extracts of rat frontal cortex and hippocampus.
FIG. 1B shows the effect of FOS and GOS on levels of NRI subunits in the rat frontal cortex and the hippocampus. Western blot images of NRI and β-actin immunoreactivity in protein extracts are shown.
Figure 1:
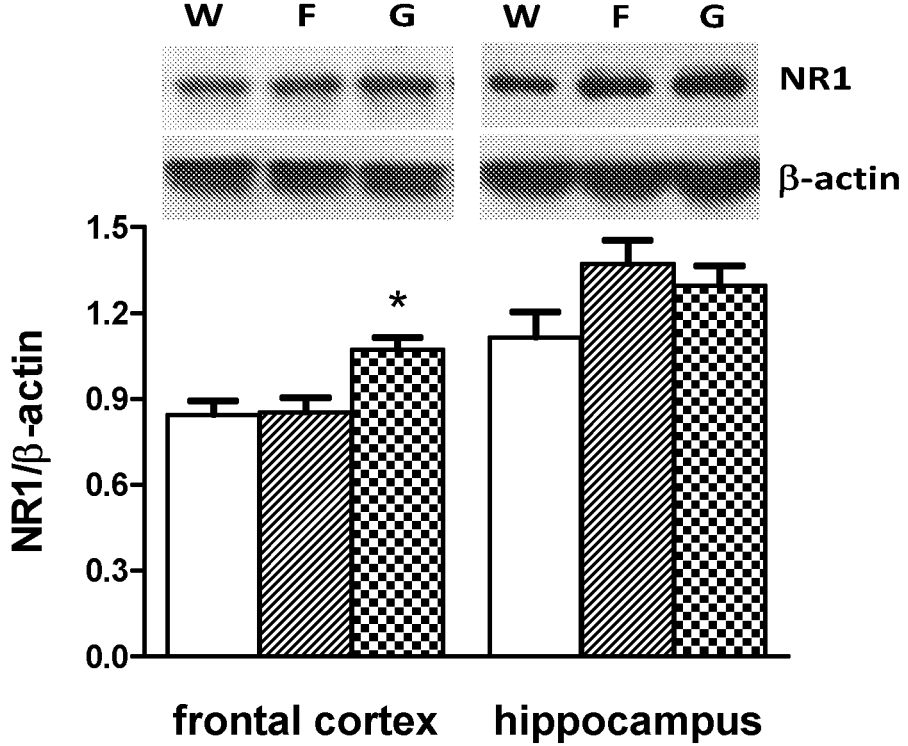

The Effect of Prebiotics on BDNF and NR1 in the Rat Frontal Cortex and Hippocampus The levels of BDNF protein in extracts of frontal cortex did not differ between groups (FIG. 1A). However, BDNF in hippocampal extracts of FOS administered rats were significantly higher than those of control and GOS fed animals. Western blots revealed that GOS-fed rats contained significantly greater levels of NR1 immunoreactivity in the frontal cortex compared to control and FOS animals (FIG. 1B). Analysis of the hippocampus, however, revealed that FOS rats contained significantly more NR1 subunits than the other groups, though an increased trend (p=0.055) was observed in GOS animals relative to controls.

Figure 2:
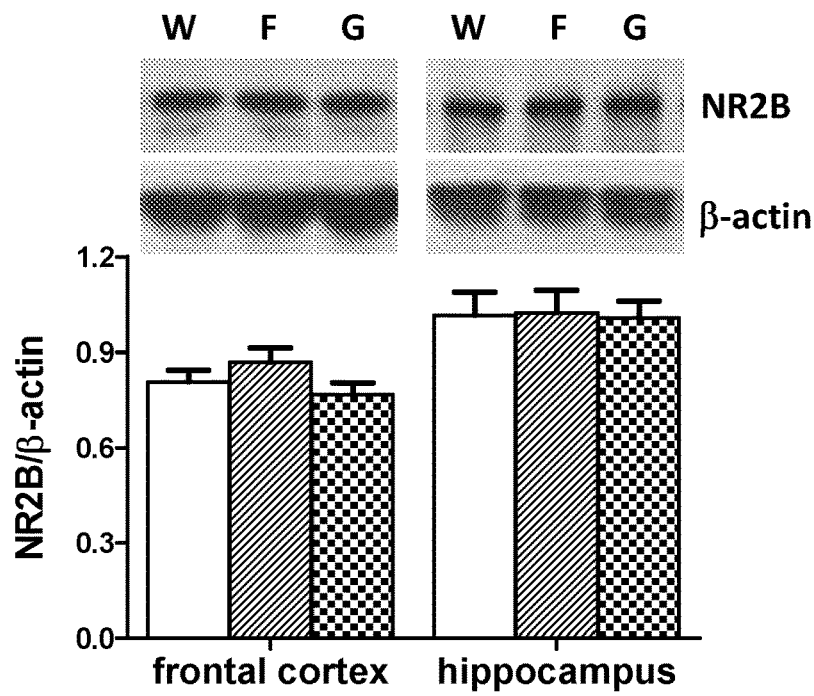
FIG. 2A shows the effect of FOS and GOS on levels of NR2A subunits in the rat frontal cortex and the hippocampus. Western blot images of NR2A subunits and β-actin immunoreactivity are shown.
FIG. 2B shows the effect of FOS and GOS on levels of NR2B subunits in the rat frontal cortex and the hippocampus. Western blot images of NR2B and β-actin immunoreactivity are shown.

The Effect of Prebiotics on NR2A and NR2B Subunits in the Rat Frontal Cortex and Hippocampus On western blots hippocampal, but not cortical, extracts from GOS-fed animals, contained significantly greater NR2A immunoreactivity compared to the other two groups (FIG. 2). The level of NR2B in the frontal cortex and hippocampus, was not affected by prebiotic feeding.

The Effect of Prebiotics on BDNF and NR Subunit mRNAs in the Hippocampus

Figure 3:
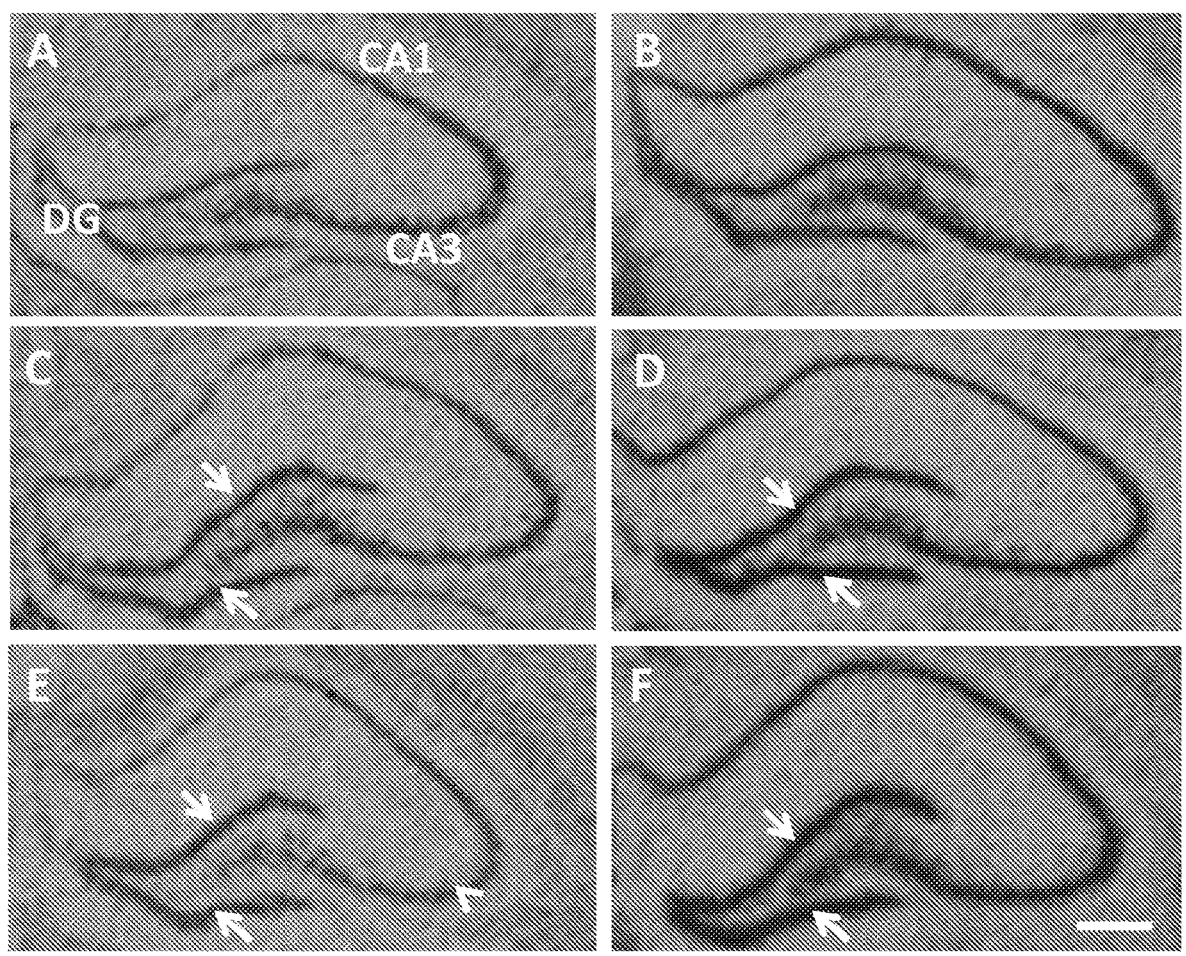
Figure 4:
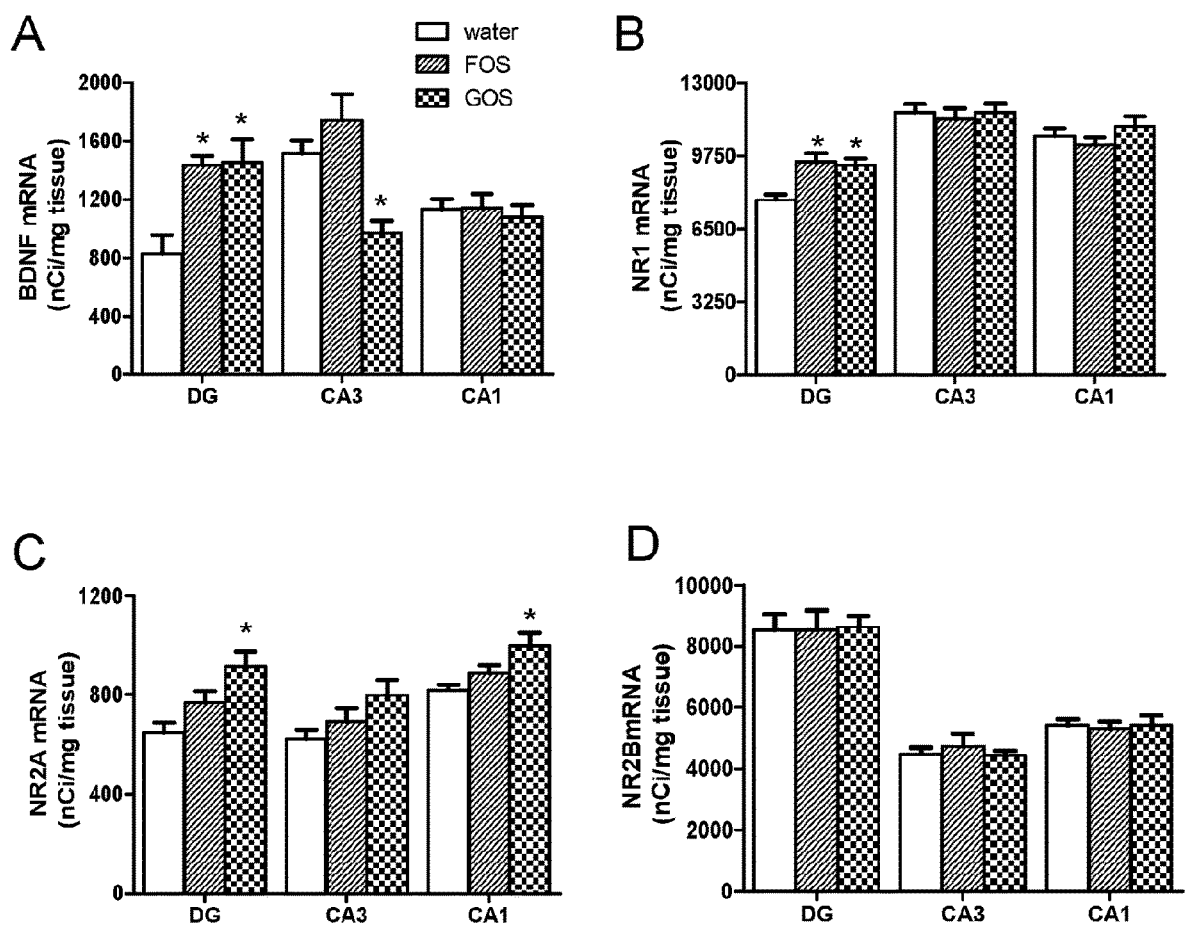

Prebiotic administration increased the abundance of BDNF (FIG. 3A, C, E and FIG. 4A) and NR1 (FIG. 3B, D, F) mRNAs in the dentate gyrus of the hippocampus, relative to controls. A reduction of BDNF mRNA in the CA3 subfield of GOS-fed rats was also observed (FIG. 3C). Densitometry confirmed significantly greater BDNF and NR1 expression in the dentate gyrus of prebiotic rats (FIG. 4A, B). The administration of GOS resulted in an elevation of NR2A (FIG. 4C), but not NR2B (FIG. 4D), mRNA in the dentate gyrus and CA1 subfield relative to controls and FOS-fed animals.

Faecal, Plasma and Brain Amino Acid Concentrations after Prebiotics

This study tested whether an elevation of gut bacteria increased central D-alanine concentrations by elevating the amounts of this D-amino acid in the gut and the circulation. The concentrations of free D-alanine in faecal pellets of GOS fed rats were significantly greater than control and FOS animals, with FOS administration resulting in intermediate levels of this D-amino acid (Table 1). Both prebiotics or GOS alone elevated other amino acids including D-serine and glutamate. In plasma D-alanine levels were significantly higher in GOS-fed rats compared to control animals (Table 1), and a slight, though not significant (p=0.086), increase was observed in FOS-fed rats. Prebiotic administration did not alter the concentrations of other circulating amino acids (Table 1). Rats fed with GOS had a significantly higher concentration of D-serine in the frontal cortex compared to controls (Table 2), though the levels of all other amino acids in both the cortex and hippocampus did not change after prebiotic feeding. There was an overall significant correlation between the levels of cortical D-serine and NR1 protein (Pearson's r=0.684, p=0.01). Individual group analysis revealed that this association was only significant after GOS feeding (GOS: r=0.96, p=0.04; FOS: r=0.68, p=0.32; water: r=0.01, p=0.989).

TABLE 1

Amino acid concentrations in rat faecal pellets and plasma following the repeated oral administration of water or prebiotic.

| Amino acid | [Amino acid] (nmol/g faeces) & (nmol/ml plasma) | | |
| --- | --- | --- | --- |
| | water | FOS | GOS |
| Faecal pellets: | | | |
| L-alanine | 7.8 ± 0.3 | 12.5 ± 0.8* | 18.7 ± 1.8*† |
| D-alanine | 4.2 ± 0.1 | 5.9 ± 0.2 | 9.0 ± 0.9*† |
| L/D-alanine | 1.9 ± 0.1 | 2.1 ± 0.1 | 2.1 ± 0.1 |
| Glutamate | 13.1 ± 1.2 | 20.9 ± 1.2 | 32.4 ± 3.4*† |
| Glutamine | 1.6 ± 0.1 | 2.8 ± 0.2* | 4.2 ± 0.4*† |
| Glut/Gln | 8.0 ± 0.2 | 7.4 ± 0.2 | 7.8 ± 0.1 |
| L-serine | 3.9 ± 0.2 | 7.0 ± 0.8 | 10.7 ± 1.1*† |
| D-serine | 0.1 ± 0.01 | 0.2 ± 0.01* | 0.2 ± 0.02* |
| L/D-serine | 39.0 ± 1.1 | 35.0 ± 2.5 | 53.5 ± 2.2* |
| Plasma: | | | |
| L-alanine | 299.9 ± 22.1 | 308.6 ± 21.8 | 310.0 ± 21.7 |
| D-alanine | 4.0 ± 0.5 | 5.2 ± 0.4 | 6.1 ± 0.5* |
| L/D-alanine | 79.2 ± 8.8 | 61.7 ± 6.9 | 49.3 ± 1.7* |
| Glutamate | 82.6 ± 6.6 | 78.9 ± 7.3 | 68.7 ± 1.6 |
| Glutamine | 419.0 ± 14.1 | 420.9 ± 18.7 | 411.2 ± 17.9 |
| Glut/Gln | 0.2 ± 0.02 | 0.2 ± 0.01 | 0.2 ± 0.01 |
| L-serine | 141.8 ± 7.8 | 142.9 ± 5.3 | 144.0 ± 6.8 |
| D-serine | 2.0 ± 0.1 | 1.9 ± 0.1 | 2.0 ± 0.1 |
| L/D-serine | 72.2 ± 2.4 | 74.5 ± 1.1 | 72.5 ± 1.6 |

*p < 0.05 compared to water;
†p < 0.05 compared to FOS

TABLE 2

Amino acid concentrations in the rat cortex and hippocampus following the repeated oral administration of water or prebiotic..

| Amino acid | [Amino acid] (pmol/mg tissue) | | |
| --- | --- | --- | --- |
| | water | FOS | GOS |
| Frontal Cortex: | | | |
| L-alanine | 90.5 ± 7.9 | 100.9 ± 8.4 | 108.6 ± 6.6 |
| D-alanine | 2.6 ± 0.4 | 2.4 ± 0.2 | 2.3 ± 0.3 |
| L/D-alanine | 37.7 ± 5.9 | 42.8 ± 3.2 | 42.2 ± 2.0 |
| Glutamate | 783.9 ± 75.6 | 837.3 ± 48.0 | 822.3 ± 47.9 |
| Glutamine | 618.9 ± 52.7 | 645.4 ± 44.7 | 700.5 ± 44.0 |
| Glut/Gln | 1.27 ± 0.06 | 1.32 ± 0.1 | 1.18 ± 0.03 |
| L-serine | 141.4 ± 13.6 | 152.8 ± 6.0 | 161.8 ± 10.9 |
| D-serine | 40.3 ± 2.9 | 48.7 ± 1.7 | 53.6 ± 3.4* |
| L/D-serine | 3.5 ± 0.23 | 3.1 ± 0.07 | 3.0 ± 0.14 |
| Hippocampus: | | | |
| L-alanine | 99.7 ± 9.5 | 92.0 ± 6.2 | 97.5 ± 9.3 |
| D-alanine | 2.8 ± 0.4 | 2.6 ± 0.2 | 2.3 ± 0.2 |
| L/D-alanine | 36.9 ± 3.9 | 36.5 ± 3.7 | 42.0 ± 2.5 |
| Glutamate | 705 ± 79.8 | 649 ± 59.3 | 643.9 ± 68.1 |
| Glutamine | 545.1 ± 58.2 | 480.1 ± 52.6 | 504.6 ± 48.0 |
| Glut/Gln | 1.30 ± 0.04 | 1.38 ± 0.09 | 1.27 ± 0.05 |
| L-serine | 121.4 ± 12.4 | 111.4 ± 7.8 | 111.9 ± 9.3 |
| D-serine | 37.4 ± 4.1 | 34.6 ± 2.1 | 35.3 ± 3.4 |
| L/D-serine | 3.3 ± 0.03 | 3.2 ± 0.04 | 3.2 ± 0.08 |

*p < 0.05 compared to water

Discussion

We observed 1) greater hippocampal BDNF levels in FOS fed rats compared to GOS fed rats and control animals, though BDNF mRNA was increased in the dentate gyrus of both FOS and GOS fed rats 2) elevated NR1 protein in the frontal cortex of GOS fed rats, and in the hippocampus of prebiotic-fed animals; 3) higher levels of NR2A protein and encoding mRNA in the hippocampus of GOS fed rats compared to the other groups. Based on the above pattern of effect it is clear that the effect of GOS is not based on its prebiotic properties but rather it is linked to the chemical structure of the saccharides in the GOS mixture.

Prebiotics Increase Hippocampal BDNF in the Rat

The elevated expression of BDNF and encoded protein in rats fed with FOS, is consistent with the effect of a *bifidobacterium* probiotic (Bercik et al; Neurogastroenterol Motil.; 23; 1132-9 (2011b); O'Sullivan et al; Benef Microbes; 2(3); 199-207 (2011)) and the selective proliferation of these species with antimicrobials (Bercik et al; Gastroenterology; 141; 599-609 (2011a)). Thus, FOS administration may have augmented the colonization of the *B. breve, B. longum* and/or similar psychotropic strains, within the moderate overall increase in bifidobacteria densities relative to GOS fed rats (see Results). In view of these observations therefore, it was surprising that GOS did not alter the levels of hippocampal BDNF protein and, moreover, by a greater magnitude than FOS. We have demonstrated that GOS feeding led to a reciprocal change in BDNF mRNA in the dentate gyrus and CA3 region of the hippocampus. An elevation of BDNF gene expression in the dentate gyrus has been associated with antidepressant action (Kerman, I. A.; Am. J. Psychiatry; 169; 1137-40 (2012)). A similar elevation of BDNF mRNA after GOS administration is, therefore, in keeping with a potential antidepressant/anxiolytic property of gut bacteria (Bercik et al, 2011a).

GOS Administration Increases NR1 Subunits in the Rat Cortex

The increased NR1 protein in GOS fed rats compared to control and FOS animals is consistent with or similar to an effect of the antidepressant, fluoxetine, a serotonin uptake inhibitor. Recent clinical studies suggest that blocking NMDARs has antidepressant effects (Autry et al; Nature; 475; 91-5; (2011)). It is clear from the data that an elevation of cortical NR1 subunits requires a several-fold increase in bifidobacteria, which occurs without changes in the levels of NR2A and NR2B subunits.

Overall, GOS administration to rats appeared to have a more profound effect on NMDAR subunits than FOS. That is, GOS elevated NR1 protein and/or mRNA in both the cortex and hippocampus, and NR2A in the hippocampus, whereas FOS only elevated NR1 in the hippocampus.

Relevance to Brain Health

Overall, our findings have some relevance to the prevention and/or treatment of cognitive dysfunction and emotional disturbances in neuropsychiatric illness and aging. For instance, patients suffering from schizophrenia show treatment-resistant deficits in executive function including working memory, in which NMDARs are integrally involved (Coyle. J. T.; Schizophr, Bull.; 38; 920-6; (2012)). The augmentation of the bifidobacteria and lactobacilli by GOS, therefore, is an important adjunctive strategy to assist contemporary pharmacological and psychological therapies. Furthermore, cognitive decline during normal aging maybe prevented or hindered by the 'prophylactic' intake of GOS, since NMDAR preconditioning has neuroprotective effects (Soriano et al; J. Neurosci.; 26; 4509-18; (2006)).

EXAMPLE 4

Human Study

Forty-five healthy volunteers received either one of two prebiotics (fructooligosaccharides [FOS] (Group A) or galactooligosaccharides [GOS] (Group C) or a placebo (Group B) (maltodextrin) for 3 weeks. Awakening salivary cortisol was sampled before and after treatment. On the final day of treatment participants completed a computerised task battery assessing the processing of emotionally salient information (the Emotional Test Battery, ETB; Harmer et al; Am. J. Psychiatry; 161; 1256-1263; (2004)).

Awakening Salivary cortisol responses did not differ significantly between groups at baseline but were significantly lower following GOS treatment compared with placebo and FOS (significant interaction between treatment group×day of sampling×sampling time point in a repeated measures ANOVA [$F(8,164)=1.20$, $p=0.05$]). Analysis of the behavioural data revealed decreased attentional vigilance to negative vs positive information after GOS compared to placebo treatment (group×emotion×masking condition, [$F(2,41)=3.14$, $p=0.05$]). The FOS treatment group did not perform differently to the placebo group in the dot-probe task. There were no significant effects of prebiotic treatment on the remaining tasks of the ETB.

Our study demonstrates that the intake of GOS lowers cortisol secretion in healthy volunteers. In addition; GOS was shown to alter the processing of positive versus negative information as measured by attentional vigilance, which is believed to play a key role in anxiety and its modulation by anxiolytics (e.g. Browning et al; J. Psychopharmacol.; 21; 684-690; Murphy et al.; Int. J. Neuropsychopharmacol.; 12; 169-179; (2009)).

EXAMPLE 5

Effect of a Mixture of Galactooligosaccharides on Lipopolysaccharide (LPS) Induced Sickness Behaviour, Post Sickness Anxiety and Altered Cytokine Levels in Mice Material and Methods
Animals, Prebiotic Administration and LPS Injections All experiments were carried out in accordance with UK Home Office Animals (Scientific Procedures) Act (1986) and under Home Office guide-lines. Male CD1 mice (25-30 g, 6-8-week old, Harlan Orlac, UK), were housed 3 per cage (plexiglas cages 33×15×13 cms, L×W×H) and maintained under standard controlled laboratories conditions (12-h light-dark cycle, lights on at 7 a.m., 21+/−1° C., humidity 50+/−5%). After 4-5 days habituation to the animal facility, mice were fed with standard mouse chow ad libitum, and provided, (in a weight-match, pseudo-random fashion), with either a prebiotic solution of 1.3% w/v mixture of galactooligosaccharides marketed commercially as Bimuno, available from Clasado Ltd. (UK), hereinafter referred to as BGOS, or water alone for drinking for 3 weeks. Pilot studies confirmed this BGOS dosing regimen optimally increased Bifidobacteria and Lactobacilli in the mouse gut (Clasado Ltd, UK). To avoid a potential cross-group contamination, the 2 diet groups were kept apart from each other. After 3 weeks, all animals received drinking water alone 24 h prior to LPS injections and behavioural tests. A single injection of LPS (0.75 mg/Kg) in saline (0.9%), or saline alone, was administered to mice by intraperitoneal injection, 4 h before behavioural tests. Four groups (n=15 mice/group, 5 different cages per treatment) were therefore tested: 1) water-fed/saline injected; 2) water-fed/LPS injected; 3) BGOS-fed/saline injected; and 4) BGOS-fed/LPS injected. This experiment was repeated to provide a total of 30 mice per test group for analysis.

Locomotor Activity (LMA)

Locomotor activity is reduced by LPS treatment (Skelly et al., (2013) PLOS One8:e69123) and thus, used as a measure of sickness behaviour. This test occurred 4 h following LPS or saline injections. The set up was made of transparent plexiglas boxes (48×27×21 cms, L×W×H, Photo Beam Activity Hardware and Software, Open Field San Diego Instruments) covered with a transparent plexiglas top (perforated for breathing) and containing a thin layer of sawdust bedding. Lighting of boxes was of about 60 lux. Each animal was gently placed at the corner of the boxes and allowed 2-h free exploration of the arena. Locomotor activity was recorded using photo-beams across the boxes and expressed as the number of break beams made by the animals over time. The number of fecal pellets was counted by the experimenter at the end of the test and animals were returned to their home cage to rest before the next behavioural testing.

Marble Burying

This test is used to screen anxiolytic and antidepressant drugs and assess anxiety and obsessive-compulsive behaviour, based on the innate behaviour of mice to bury objects in a stressful situation; it was conducted as previously described (Deacon R. M.; Nat. Protoc.; (2006); 1 (1); 122-124, Nicolas et al.; Eur. J. Pharmacol.; (2006); 547; 106-115). LPS treatment, and the related LPS-induced sickness behaviour, induce a reduction in the number of marbles buried by the mice (Njung'e & Handley; Pharmacol. Biochem. Behav.; (1991); 38 (1); 63-67). Marble burying was conducted 7 h following LPS/saline injection. Twenty marbles were placed on top of 5-cm sawdust bedding in transparent plastic cages (44×28×12 cms, L×W×H), in 5 lines of 4, 2 cms away from each other and 2 cms away from the edge of the cages. Testing occurred under normal room lighting, (~100 lux at 1 m above the floor) and as previously described (Treit, D. et al.; Pharmacol. Biochem. Behav.; 1981; 15 (4); 619-626) and using the recommendations from (Deacon, R., 2006). Each animal was gently placed in the cage with the marbles for 30 min, after which the number of marbles buried to at least ⅔ of their surface was counted.

Light-Dark Box

This test is also used to assess anxiety behaviour and based on the conflict mice face between their attraction for novelty and their fear for bright open arenas (Bourin, M. and Hascoet, M.; Eur. J. Pharmacol. (2003); 463 (1-3); 55-65; O'Leary, T. P. et al; J. Neuroscience Methods; (2012); 203; 315-324. doi: S0165-0270 (11) 00594-21). Mice that are less anxious spend more time in fearful areas, i.e. the light part; mice that are more anxious spend more time in the safe dark part. LPS treatment has been shown to increase anxiety behaviour in this test (Bassi et al; Basic Clin. Pharmacol. Toxicol.; (2012); 110 (4); 359-369). This test was conducted 24 h following LPS/saline injections.

The set up was made of 2 painted wood compartments, a small black one (21×16×16 cms, L×W×H, with a small opening for access to the light part, 3×2.7 cms, W×H) and a bigger bright one (46.5×21×21 cms, L×W×H). Testing occurred under a slightly dim light of 50 lux inside the bright compartment of the box and was conducted as previously described (Strekalova T. et al.; Neuropsychopharmacology; (2004); 29; 2007-2017). Each animal was gently placed in the dark part of the light-dark box and let free to explore the whole box for 5 min. The latency to leave the dark part, number of transitions between the dark and lights parts and the time spent in the light part were measured. The criterion to enter any compartment was 4 paws in. Mice were placed back to their home cage with cage mates at the end of the procedure. The box was cleaned with a tissue slightly impregnated with 10% alcohol between each animal in order to remove odour cues without creating overt alcohol odours. There was no background noise in the room and the experimenter stayed in the room for live scoring. Animals are deemed more anxious, and thus, affected by LPS injection, if they display a higher latency to enter the light part, a lower number of transitions between compartments and a lower time in the light area.

Tissue Collection

Animals were sacrificed between 12-1 p.m., 3 h following behavioural testing. Whole brain was immediately harvested and snap-frozen in cold isopentane on dry-ice (Sigma-Aldrich, UK) before storage at −80° C. until further molecular analysis. Trunk blood was collected in potassium EDTA (Ethylene Diamine Tetra Acetic Acid) tubes and spun for 15 min at 5000 rpm. Plasma was isolated and stored at −80° C. for further corticosterone analysis. Fecal pellets were collected from each cage throughout the study in 70% glycerol in PBS (phosphate buffered saline) and stored at −20° C. for further bacterial count.

Data Analysis

Data were analysed using SPSS software (version 19). Data normality was tested using a Kolmogorov-Smirnov test. Locomotor activity was assessed with a 2-way ANOVA, and all other data with one-way ANOVA (or Kruskal-Wallis for non-parametric data) followed by Tukey post-hoc test. All data are expressed as mean±standard error of the mean (SEM) and the threshold for statistical significance was set at $p<0.05$.

Results

Effects of BGOS on the Immediate LPS-Induced Sickness Behaviour: Locomotor Activity and Marble Burying Water-fed animals displayed a lower locomotor activity following LPS injections, compared with saline (FIG. 6A, time effect, $F(5,260)=142.12$, $p<0.0001$; LPS injection effect $(F(1,52)=3.61$, $p=0.063$; interaction time×LPS injection $F(5,260)=5.12$, $p<0.001$). Post-hoc test revealed that water-LPS animals travelled significantly less distance than their saline counterparts at 30 and 40-min time-points (both $p<0.05$). BGOS abolished LPS effect on locomotor activity (FIG. 6B) as there was still an effect of time $(F(5,260)=113.01$, $p<0.0001)$, but no effect of LPS injection $(F(1,52)=1.12$, $p=0.3)$ and no interaction time×LPS injection $(F(5,260)=0.12$, $p=0.99)$. BGOS did not induce any difference in locomotor activity in saline animals compared with water saline group.

In the marble burying test (FIG. 7), LPS had a significant effect on mice behaviour $(H(df=3)=13.79$, $p<0.01)$, which was not reversed by BGOS, as both water $(p<0.05)$ and BGOS $(p<0.05)$-treated animals which received LPS buried less marbles than their saline counterparts. BGOS did not induce any difference in the number of marbles buried in saline animals, compared with water saline group.

Effects of BGOS on the Delayed LPS-Induced Anxiety Behaviour: Light/Dark Box

LPS increased anxiety behaviour in water-fed animals (FIG. 8). This effect was abolished by BGOS, as assessed by the latency to light (FIG. 8A, $H(df=3)=12.17$, $p<0.01$) and time in light (FIG. 8B, $F(3,106)=4.71$, $p<0.01$). Indeed, post-hoc analysis revealed that water-LPS animals displayed a significantly 2-fold higher latency to light than their saline counterparts ($p<0.01$) but also than both saline- and BGOS-LPS animals (both $p<0.05$). Water-LPS animals also displayed significantly less time in the light part than all the other groups ($p<0.05$ water-LPS vs. all groups). However, there was no statistical difference between groups in the number of transitions between the dark and light parts (FIG. 3C, $F(3,110)=1.7$, $p=0.17$). BGOS alone did not induce any difference in control mice, i.e. which received saline, in any of the parameters, compared with water-saline animals.

Effects of BGOS on Immune Parameters 24 h Post LPS: Cytokines Levels in the Frontal Cortex and Plasma In the frontal cortex, LPS induced changes in water, but not BGOS, animals (FIG. 9) for TNF-α, IL-1β and IL-6, but not for IL-10. Post-hoc analysis showed that water LPS animals displayed higher TNF-αα than all other groups (p<0.05), higher IL-1β (p<0.01 vs. water saline and vs. BGOS saline, p<0.05 vs. BGOS LPS) and higher IL-6 (p<0.05 vs. water saline). Thus, cytokines levels for animals fed with BGOS, receiving either saline or LPS injection, were both similar to those of their control water saline counterparts.

In the plasma, LPS induced significant changes in water, but not BGOS, animals (FIG. 10) for TNF-α, however there was no overall statistical difference between groups for IL-6 and IL-10, as well as IL-1β, although for this latter, LPS induced a non-significant 2-fold increase in water animals compared with saline.

Discussion

The current study tested the influence of prebiotic (BGOS) intake on LPS-induced sickness behaviour, anxiety and cytokine expression in mice, and was based on the supposition that BGOS (Bimuno) affects brain function via the immune system. Our two key findings were: 1) BGOS fed mice did not manifest locomotor activity (LMA) deficits and anxiety after a single injection of LPS, compared to controls; and 2) the LPS-induced expression of pro-inflammatory mediators in the plasma (Granulocyte colony-stimulating factor (G-CSF); chemokine (C-C motif) ligand 2 (CCL2); monokine induced by IFNγ, Chemokine (C-X-C motif) Ligand 9 (MIG)) and brain (TNFa) was suppressed by the ingestion of BGOS. Overall, our data support current notions that BGOS (Bimuno) plays an important role in the maintenance of brain health, and that a modification in the response to immune challenges, may underpin this action.

EXAMPLE 6

Effect of BGOS on Cognitive Performance in Healthy Rats

Materials & Methods

Normal Sprague Dawley rats were given water or a prebiotic solution of 1.3% w/v mixture of BGOS for 3 weeks and then tested on the attentional set-shifting task (ASST) (see Bissonette, G. B. et al; Behavioural Brain Research; (2013); 250; 91-101) using standard protocols.

Results

FIG. 11 shows that rats given BGOS for 3 weeks showed improved performance in the extra-dimensional (ED) component of the ASST that is a measure of flexible learning. Execution of the ED element as effortlessly as the intra-dimensional phase (ID/ED-shift) is indicative of increased cognitive flexibility, a parameter which is impaired in the elderly. In FIG. 11 #p<0.05 compared to control ID and *p<0.05 compared to control ED.

CONCLUSION

Rats given BGOS show improved cognitive performance in a task dependent on the medial prefrontal cortex, which is often impaired in psychiatric disorder and ageing.

The invention claimed is:

1. A method of reducing cortisol secretion in a subject suffering from depression, the method comprising administering to the subject suffering from depression an effective amount of a galactooligosaccharide composition comprising disaccharides Gal (β1-3)-Glc; Gal (β1-3)-Gal; Gal (β1-6)-Gal; Gal (α1-6)-Gal; trisaccharides Gal (β1-6)-Gal (β1-4)-Glc; Gal (β1-3)-Gal (β1-4)-Glc; tetrasaccharide Gal (β1-6)-Gal (β1-6)-Gal (β1-4)-Glc and pentasaccharide Gal (β1-6)-Gal (β1-6)-Gal (β1-6)-Gal (β1-4)-Glc, wherein the effective amount of the galactooligosaccharide composition is administered daily as two separate doses administered from 4 to 12 hours apart, and wherein the effective amount of the composition comprises 2.7 to 2.75 g of galactooligosaccharides in 3.0 to 5.5 g of the composition or comprises 2.7 g to 2.75 g of galactooligosaccharides in 4.1 g to 7.25 g of the composition.

2. The method according to claim 1, wherein the subject is a human.

3. The method according to claim 1, wherein the composition is administered orally.

4. The method according to claim 1, wherein the effective amount of the galactooligosaccharide composition is administered daily as two separate doses administered from 6 to 10 hours apart, or from 8 hours apart.

5. The method according to claim 1, wherein the composition is in the form of a powder, a tablet, a capsule, or a liquid.

6. The method according to claim 5, wherein the liquid is a syrup formulation.

7. The method according to claim 5, wherein the liquid is a dried syrup forming a soft pastille.

8. The method of claim 1, wherein the method increases brain derived neurotrophic factor (BDNF) in dentate gyrus of the subject suffering from depression.

9. A method of increasing brain derived neurotrophic factor (BDNF) in dentate gyrus of a subject suffering from depression, the method comprising administering to the subject suffering from depression an effective amount of a galactooligosaccharide composition comprising disaccharides Gal (β1-3)-Glc; Gal (β1-3)-Gal; Gal (β1-6)-Gal; Gal (α1-6)-Gal; trisaccharides Gal (β1-6)-Gal (β1-4)-Glc; Gal (β1-3)-Gal (β1-4)-Glc; tetrasaccharide Gal (β1-6)-Gal (β1-6)-Gal (β1-4)-Glc and pentasaccharide Gal (β1-6)-Gal (β1-6)-Gal (β1-6)-Gal (β1-4)-Glc, wherein the effective amount of the galactooligosaccharide composition is administered daily as two separate doses administered from 4 to 12 hours apart, and wherein the effective amount of the composition comprises 2.7 to 2.75 g of galactooligosaccharides in 3.0 to 5.5 g of the composition or comprises 2.7 g to 2.75 g of galactooligosaccharides in 4.1 g to 7.25 g of the composition.

10. The method according to claim 9, wherein the subject is a human.

11. The method according to claim 9, wherein the composition is administered orally.

12. The method according to claim 9, wherein the effective amount of the galactooligosaccharide composition is administered daily as two separate doses administered from 6 to 10 hours apart, or from 8 hours apart.

13. The method according to claim 9, wherein the composition is in the form of a powder, a tablet, a capsule, or a liquid.

14. The method according to claim 13, wherein the liquid is a syrup formulation.

15. The method according to claim 13, wherein the liquid is a dried syrup forming a soft pastille.

* * * * *